United States Patent [19]

Davison et al.

[11] Patent Number: 4,862,878
[45] Date of Patent: Sep. 5, 1989

[54] ORTHOPEDIC PROSTHESIS TO AID AND SUPPORT THE SHOULDER MUSCLES IN MOVEMENT OF THE HUMAN ARM

[75] Inventors: Steven W. Davison, Newnan, Ga.; William D. McLeod, Memphis, Tenn.

[73] Assignee: Richards Medical Company, Memphis, Tenn.

[21] Appl. No.: 141,594

[22] Filed: Jan. 7, 1988

[51] Int. Cl.$^4$ .......................... A61F 5/00; A61F 5/01; A61F 5/02

[52] U.S. Cl. ........................................ 128/77; 128/78; 2/44; 2/45

[58] Field of Search ............... 128/DIG. 19, 78, 87 R, 128/77, 95.1, 99.1–111.1, 25 R, 26, 88, 83, 87 C; 623/58; 2/44, 45

[56] References Cited

U.S. PATENT DOCUMENTS

| | | | |
|---|---|---|---|
| 559,024 | 4/1896 | Bessing | 2/45 |
| 3,499,441 | 3/1970 | Hall | 2/44 |
| 3,906,944 | 9/1975 | Christen | 2/45 |
| 4,180,870 | 1/1980 | Radulovic et al. | 128/77 |
| 4,559,932 | 12/1985 | Salort | 128/77 |
| 4,644,939 | 2/1987 | Coleman | 128/78 |

*Primary Examiner*—Edgar S. Burr
*Assistant Examiner*—Kimberly L. Asher
*Attorney, Agent, or Firm*—Pravel, Gambrell, Hewitt, Kimball & Krieger

[57] ABSTRACT

An orthopedic prosthesis including a trunk engaging means, an arm engaging means and a lift assist means. The trunk engaging means includes a shoulder engaging means comprised of a strap which passes over the injured shoulder and a support plate attached to each end of the shoulder strap, the support plates being positioned in front of and behind the shoulder to be supported. The trunk engaging means also includes a lateral support strap, one end of the strap being connected to one of the support plates and around the body of the wearer under the arm opposite of the shoulder to be supported where it is connected to the second support plate. The arm engaging means includes a strap passing around the humerus of the arm of the wearer. The lift assist means utilizes two pulley systems, one mounted on the arm engaging means and one on the support plate of the shoulder engaging means. The lift assist means further includes an elasticized cord anchored to the arm engaging means which passes, in order, through the shoulder pulley system, the arm pulley system and is anchored on the other support plate. The elastic cord is in tension when the wearer's arm is at the side of the body. As the arm is raised, the energy stored in the arm is transferred through the pulley system, which operates as a variable lever, to the shoulder muscles thereby aiding in the lifting of the arm up and away from the side of the wearer throughout a full range of locations of the arm relative to the wearer's body, and at the same time allow unrestricted lateral movement of the arm.

13 Claims, 4 Drawing Sheets

ORTHOPEDIC PROSTHESIS TO AID AND SUPPORT THE SHOULDER MUSCLES IN MOVEMENT OF THE HUMAN ARM

BACKGROUND OF THE INVENTION

1. Field of the Invention

The present invention relates to orthopedic prostheses designed to support muscles in the human shoulder and, more particularly, to such a prosthesis designed to reduce the strain on shoulder muscles during a full range of arm movements by aiding movement of the arm.

2. General Background

The human shoulder is particularly susceptible to pull, tear and strain of certain muscle groups and connecting tendons and ligaments. These injuries lead to decreased function of the shoulder during the period of recovery and, in severe cases, can result in a permanent decrease in shoulder function. The decrease in function may occur as a result of a traumatic incident such as a muscle or ligament tear, or may occur as a result of disease or atrophy of the shoulder muscles due to age or other causes. Such injuries are particularly serious for athletes who rely on arm and shoulder movement in order to perform. When there is a slight tear or pull, an athlete should refrain from any strenuous activity. Attempts to make the shoulder function at previous levels of performance before a total recovery can often result in re-injury or an aggravation of the injury.

A common approach in dealing with this tendency to re-injure the shoulder muscles has been to deliberately restrict movement during the recovery or healing period. A number of devices have been designed to restrict movement during this period. Examples of such devices include those described in the following U.S. patents.

U.S. Pat. No. 3,906,944 describes a shoulder harness which limits the range of arm movement to less than 90 degrees away from the body by limiting the degree to which shoulder muscles abduct or contract.

U.S. Pat. No. 4,644,939 describes a shoulder brace for limiting and guiding movement of the arm as it is raised from the wearer's side. An elasticized brace is described as limiting upward movement of the arm by "anchoring" the upper arm to the wearer's body through an elasticized web. The web applies tension on the upper arm, which is described as limiting the arm's movement and guiding the humerus in its movement within the shoulder socket.

U.S. Pat. No. 3,499,441 also describes an elasticized brace which restricts movement through use of elastic bands surrounding the shoulder, limiting both lateral movement of the shoulder and the range of movement of the arm from the wearer's side.

U.S. Pat. No. 559,024 describes an elasticized body brace that includes woven and elastic material for limiting the range of movement of the arm and shoulder.

None of the above devices included any features that actually aid in arm movement. One device that does aid movement of the arm is described in U.S. Pat. No. 4,180,870 where a wearer harness and pneumatic energizing means helps the wearer lift his or her arm through a system of levers and eccentric cams for articulating the arm toward and away from the body of the wearer. While this device assists in movement of the shoulder, arm and wrist, it is a cumbersome device to wear, expensive to manufacture and has the effect of limiting rate of movement to a predetermined rate of movement of a hydraulic cylinder.

SUMMARY OF PRESENT INVENTION

The present invention is directed toward an improved orthopedic orthosis designed to aid and support the shoulder muscles during movement. As the arm is raised or otherwise moved from the wearer's side, the shoulder muscles abduct, or contract, which causes the arm to be moved into a desired position.

The present invention includes a body engaging support, which is made up of a lateral strap that engages the chest and back of the wearer and extends around the side of the wearer opposite the shoulder to be supported. A vertical shoulder strap passes over the shoulder to be supported and is connected to the lateral strap in front of and behind the shoulder to be supported.

An arm support strap is worn on the biceps of the arm of the shoulder to be supported, which is connected to the body support through a resilient cord or other stored energy source which can supply varying amounts of applied force to the arm, depending on the type of movement desired. The varying amounts of force are supplied by connecting the cord to both the front and back of the body support and to the arm through a guide in the form of a lever and/or pulley system that is mounted on the arm support.

This construction aids in the movement of the arm away from the wearer's side by decreasing the degree to which the shoulder muscles are required to abduct in lifting the arm. The guide allows the arm to have a full range of movement without any restrictions due to built in limits of the stored energy source.

The present invention is directed toward aiding and supporting the movement of the human shoulder, including raising the arm more than 90 degrees away from the side of the body. In doing so, the present invention provides a device that is light in weight and relevatively inexpensive to make. The invention does not limit the rate or the range of movement of the wearer during use of the device.

Further, the invention is designed to aid the muscles of the shoulder to achieve a functional efficiency similar to that enjoyed prior to injury and may continue to be used following the recovery period to help overcome any permanent loss in shoulder function.

DETAILED DESCRIPTION OF AN EXEMPLARY EMBODIMENT

Figure 1:
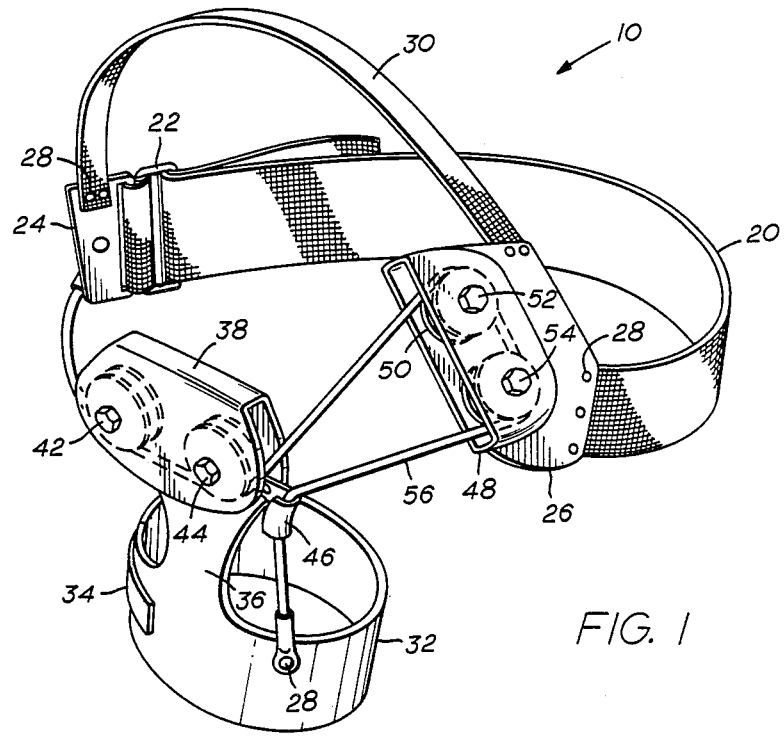
FIG. 1 is a perspective view showing an exemplary embodiment of the invention.

Referring to FIG. 1, an orthopedic orthoses 10 made in accordance with the invention includes a flexible lateral strap 20 which is designed to encircle the chest and back of the wearer (shown in FIGS. 2-7). The strap 20 passes under the arm of a shoulder on the side of the wearer opposite the one to be supported by the invention. The strap 20 may be adjusted to more closely fit the wearer by means of an adjustment buckle 22 positioned on a first end 58 of the strap 20. Although the preferred embodiment shows the adjustment buckle 22 as having a clamping mechanism, other types of buckles or holding mechanisms could be used.

The strap 20 is designed to provide lateral body support while the orthosis 10 is in use. The strap 20 includes first and second ends 58 and 60, that are connected to rigid support plates, 24 and 26, respectively, which are positioned in front of and behind the shoulder of the wearer. The support plates 24 and 26 are connected to the first and second ends 58 and 60 of the lateral strap 20 by means of rivets 28 or other similar securing means.

The orthosis 10 engages the shoulder to be supported through a shoulder support member 30, which is designed to pass over the shoulder of the wearer to be supported. The vertical support member 30 is made of a suitable flexible or rigid material, such as lightweight metal or plastic. The shoulder support 30 is connected to the support plates 24 and 26 by means of rivets 28 or other similar securing means.

An arm strap 32 is positioned and worn on the biceps of the arm of the shoulder to be supported (see FIGS. 2-7). The arm strap may be constructed of any suitable flexible or semi-rigid material and can be adjustable to fit the arm of the wearer by means of an arm adjustment band 34, which includes hook and loop fasteners or discrete notches as shown in FIG. 1. One end of an arm extension piece 36 is connected to the arm strap 32, which is positioned on the outer side of the arm of the wearer when the orthosis is in use.

In the embodiment of the invention as shown, the arm extension piece 36 is part of a unitary construction which includes the adjustable arm strap 32, arm extension piece 36 and a pulley housing 38 which is connected to the end of the arm extension piece 36 opposite the strap 32. The pulley housing 38 includes first and second pulleys which are mounted within the pulley housing 38 by means of bolts 44 and nuts 42. A hollow guide 46 is also mounted in the pulley housing 38 for guiding movement of a lifting aid which is described in greater detail below.

A second pulley housing 48 is mounted on the support plate 26 that is connected to the end 60 of lateral strap 20. The second pulley housing 48 is rigid and formed as an integral part of the support plate 26. One or more pulleys 50 are mounted within the second pulley housing 48 through nuts 52 and bolts 54.

The pulleys 50 act in the capacity of an adjustable lever system and can be replaced by a lever. The net effect of the pulley/lever system is to sense arm elevation and increase the tension in the elastic member 56 as the arm is elevated. This effectively compensates for the natural shortening if the distance between support plates 24 and 26 and the arm pulley housing 38 to provide support of arm elevation function throughout the range of motion.

In the preferred embodiment, a single elastic cord 56 under tension is used as a lifting means to aid movement of the arm to be supported. One end of the elastic cord 56 is secured to the arm strap 32 through a rivet 28 or other suitable device. The elastic cord 56 passes through the guide 46 and extends to the second pulley housing 48, over the second pulleys 50. The elastic cord 56 then extends to the first pulley housing 38 and passes over the first pulleys 40. The elastic cord 56 then extends over to the support plate 24 where it is secured by means of a rivet 28 or other suitable device.

Figure 2:
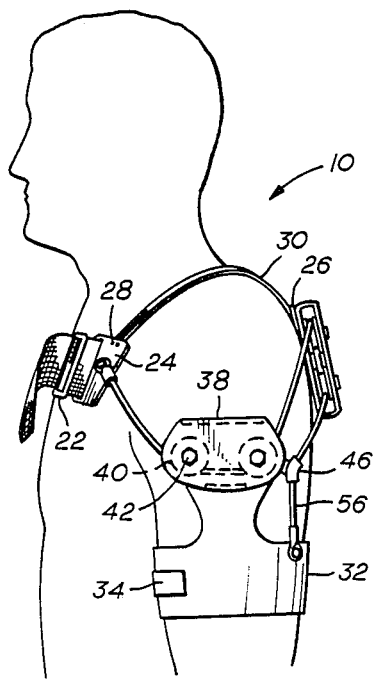
FIG. 2 is a side view showing the invention being worn by a wearer, from the side of the shoulder of the wearer to be supported.
Figure 3:
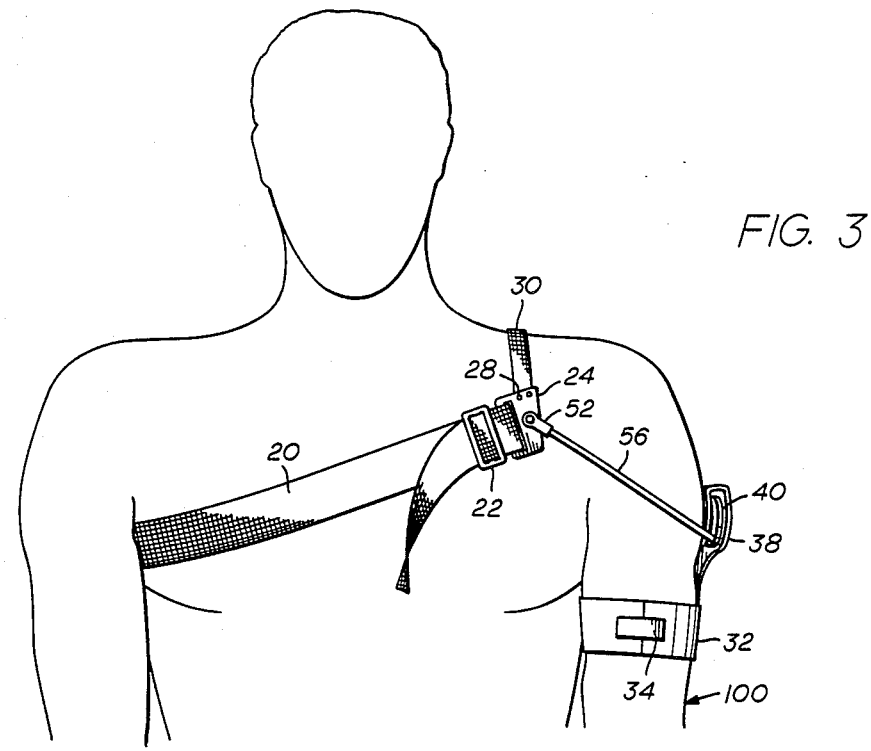
FIG. 3 is a partial front view showing the invention being worn by the wearer, with the arm at the wearer's side.
Figure 4:
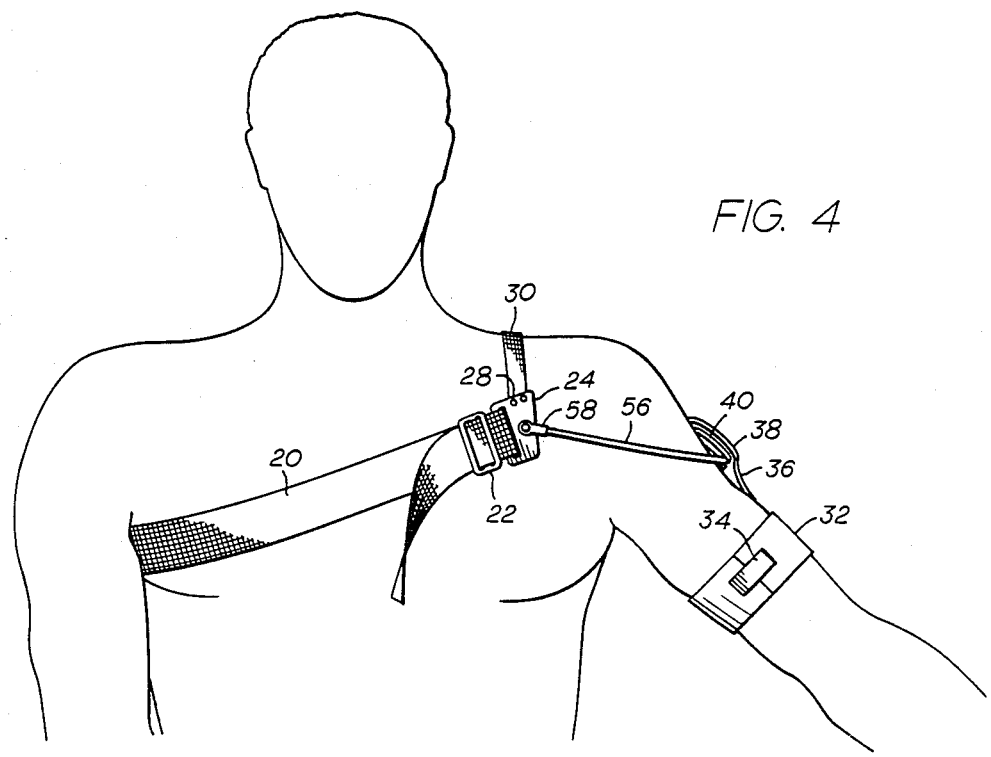
FIG. 4 is also a partial front view as in FIG. 3, showing the arm lifted away from the wearer's side.
Figure 5:
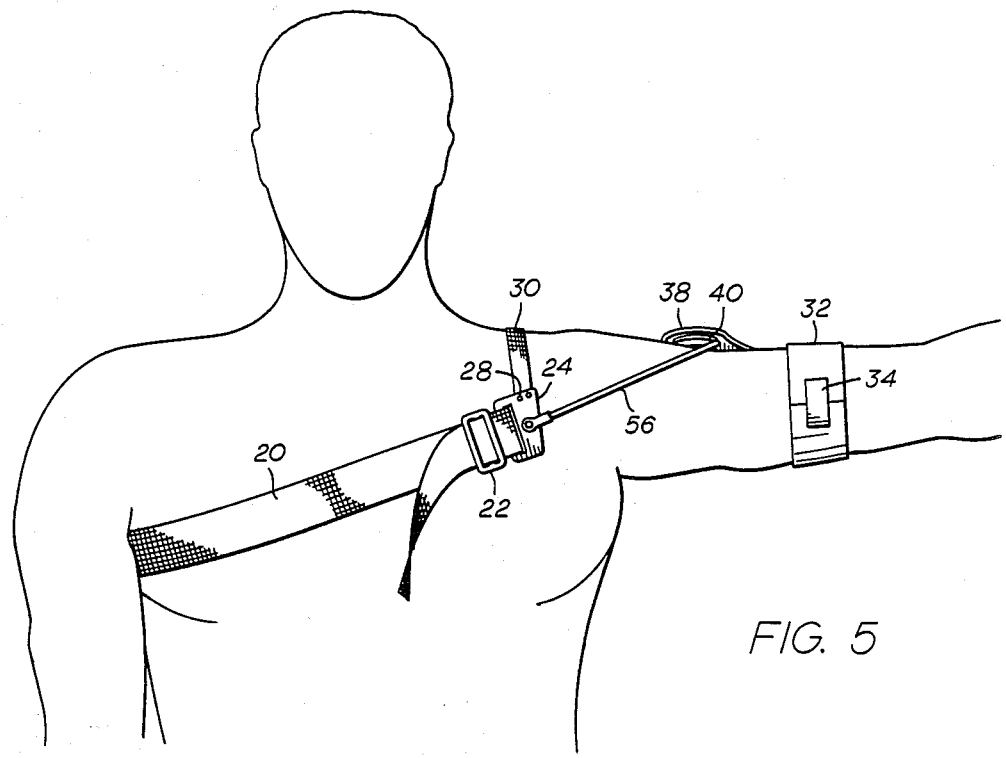
FIG. 5 is also a partial front view as in FIG. 3, showing the arm raised to about 90 degrees away from the wearer's side.

FIG. 2 shows the orthosis 10 being worn by the wearer whose shoulder muscles and arm are to be supported, as described in detail below. FIGS. 3-5 are sequential front views of the orthosis 10 shown in operation. Referring to FIG. 3, when the arm 100 of the wearer is at rest by the wearer's side, the muscles of the shoulder deltoid group 130, pectoralis major 150, trapezius 160, upper arm biceps 110, and brachialis anticus 120, are in a relaxed, extended position. At the same time, the elastic cord 56 of the prosthesis 10 is under tension. As the arm is raised, as shown in FIG. 4, the muscles of the shoulder deltoids 130, pectoralis major 150, trapezius 160, upper arm biceps 110, and brachialis anticus 120, begin to abduct or contract. It is this contraction which places a strain on the various muscles and tendons in the shoulder and arm.

As the arm 100 is lifted, the stored energy in the elastic cord 56 causes it to contract and exert a lifting force on the arm 100. This lifting force aids the muscles of the arm and shoulder in lifting the arm. Since the elastic cord 56 passes over the pulley systems 40 and 50, the lifting force exerted by the elastic cord 56 is distributed evenly on both sides of the shoulder regardless of whether the arm 100 is lifted straight up or down or whether it is moved to the front or back of the wearer. When the arm is lifted to the position shown in FIG. 5, the muscles of the shoulder deltoids 130, pectoralis major 150, trapezius 160, upper arm biceps 110, and brachialis anticus 120 plus the superior rotator cuff muscles are in a highly contracted state and the elastic cord 56 has approached the position where most of its stored energy has been expended.

Figure 6:
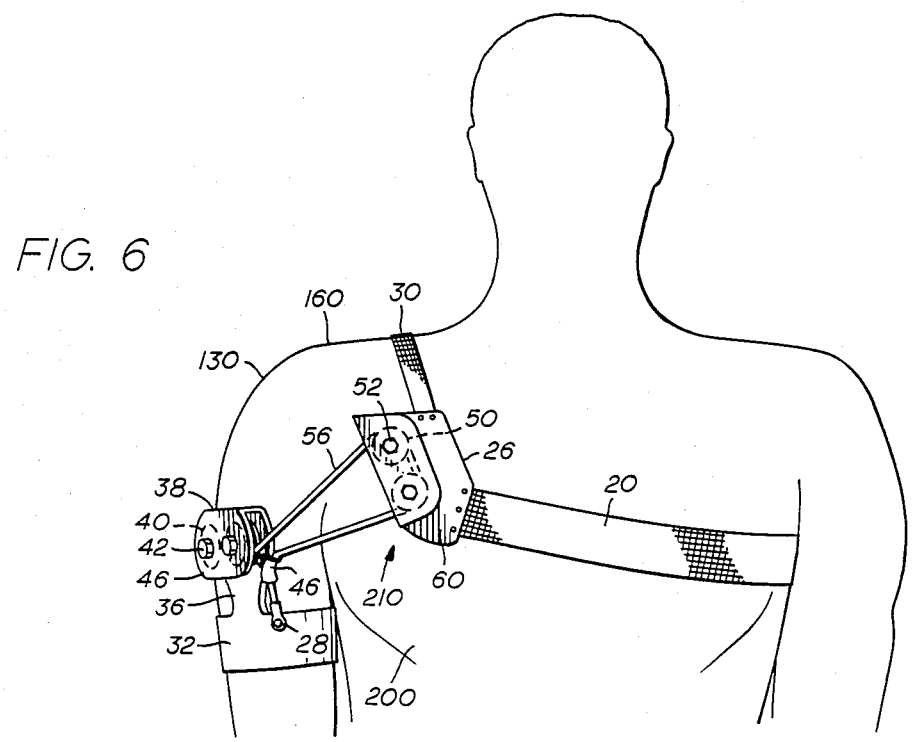
FIG. 6 is a partial rear view showing the invention, with the arm at the wearer's side.
Figure 7:
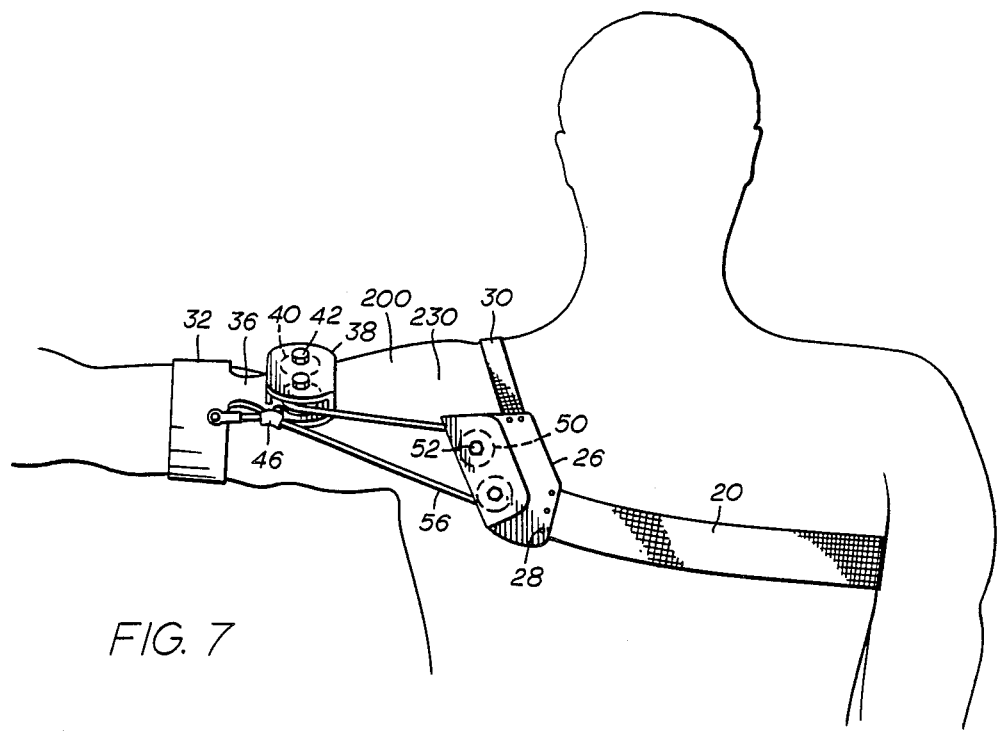
FIG. 7 is also a partial rear view as in FIG. 6, showing the wearer's arm in a raised position.

FIGS. 6 and 7 show the muscle groups and orthosis 10 from the rear of the wearer. In FIG. 6, the arm 100 is relaxed and at the side of the wearer. The muscles of the shoulder deltoid group 130, triceps 160, back infraspinitus 200, teres major 210, trapezius 230 and latissimus dorsi 220 are shown in their relaxed, extended positions. The elastic cord 56 of the orthosis 10 is shown in a stretched position. As the arm is raised, as shown in FIG. 7, these muscles abduct, lifting the arm 100. During this movement, the orthosis 10 aids in this process by transferring energy stored in the stretched elastic cord 56, as shown in FIG. 6, to the muscles of the shoulder and the back, thereby aiding in lifting the arm.

By utilizing the energy in the elastic cord 56, the arm 100 can be raised with the help of the elastic cord 56, which has the effect of reducing strain on the muscle groups mentioned above. This reduction in strain allows the wearer to perform physical acts that otherwise would aggravate an injury to those muscles if assistance was not provided as described.

It will be appreciated that the various structural members that make up the orthopedic orthosis 10 can be formed in numerous different embodiments without departing from the teachings of the present invention. The foregoing disclosure and description of the invention are illustrative and explanatory of the invention and are not intended to be limiting as to the scope of the invention.

I claim:

1. An orthopedic orthosis for supporting the human shoulder muscles during movement of the arm, comprising:
   (a) a body engagement means, including a trunk engaging means comprising a lateral support means for engaging the chest and back of the wearer and extending around a side of the wearer opposite the shoulder to be supported, a shoulder engaging means for engaging the shoulder of the wearer to be supported, and means for connecting the shoulder engaging means to the trunk engaging means at both the chest and back sides of the wearer;
   (b) arm engaging means to engage the upper arm of the shoulder to be supported above the elbow; and
   (c) lift assist means for directly connecting the trunk engaging means to the arm engaging means, the assist means including means for reversibly storing energy and applying the stored energy to the arm to aid in the movement of the upper arm up and away from the side of the wearer throughout a full range of locations of the arm relative to the wearer's body, and at the same time allow unrestricted lateral movement of the arm, the direction and rate of the force applied by the assist means being controlled by the natural movement of the arm.

2. The orthopedic orthosis of claim 1, wherein the lateral support means includes a flexible lateral strap which extends from the chest to the back side of the wearer.

3. The orthopedic orthosis of claim 2, wherein, the flexible lateral strap includes first and second ends, at least one end being adjustable in length so that the ends can be positioned in front of and behind the shoulder to be supported.

4. The orthopedic orthosis of claim 3, further including a rigid support plate at both the first and second ends, the shoulder engaging means and lift assist means being connected to both support plates.

5. The orthopedic orthosis of claim 1, wherein the shoulder engaging means includes a strap formed of flexible material.

6. The orthopedic orthosis of claim 1, wherein the shoulder engaging means is formed of a semi-rigid material formed to the curve of the shoulder of the wearer.

7. The orthopedic orthosis of claim 1, wherein the arm engaging means includes a flexible strap which encircles and can be positioned on the arm of the wearer above the elbow.

8. The orthopedic orthosis of claim 7, wherein the arm strap is formed of a semi-rigid material formed to the curve of the upper arm of the wearer.

9. The orthopedic orthosis of claim 4, wherein the lift assist means includes tensioning means connecting the back and front sides of the trunk engaging means with the arm engaging means.

10. The orthopedic orthosis of claim 9, wherein the tensioning means includes at least one elastic cord.

11. The orthopedic orthosis of claim 10, wherein the tensioning means includes a single elastic cord having first and second ends.

12. The orthopedic orthosis of claim 11, wherein the means for connecting the lift assist means to the trunk engaging means and arm engaging means comprises:
    (a) a first pulley means mounted on the first rigid support plate of the shoulder engaging means;
    (b) a second pulley means mounted on the arm engaging means;
    (c) a guide means mounted on the arm engaging means;
    (d) the elastic cord, having its first end anchored to the arm engaging means, the second end of the elastic cord passing through the guide means on the arm engaging means, through the first pulley means mounted on the first rigid support means, through the second pulley means mounted on the arm engaging means, the second end of the elastic cord then being anchored to the second rigid support plate of the shoulder engaging means.

13. The orthopedic orthosis of claim 12, wherein the first and second pulley means each includes a pair of pulleys.

* * * * *